United States Patent
Suzuki et al.

(10) Patent No.: US 6,384,237 B1
(45) Date of Patent: May 7, 2002

(54) PYRYLIUM COMPOUND, PROCESS FOR MAKING THE SAME, NUCLEIC ACID STAIN, AND LABELED NUCLEIC ACID

(75) Inventors: Tomohiro Suzuki; Tadashi Okamoto; Nobuko Yamamoto, all of Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/621,668

(22) Filed: Jul. 24, 2000

(30) Foreign Application Priority Data

Jul. 23, 1999 (JP) .......................... 11-209828

(51) Int. Cl.[7] ..................... C07D 309/34; C07D 335/02
(52) U.S. Cl. .................... 549/13; 549/426; 549/427; 549/428
(58) Field of Search ................ 549/13, 426, 427, 549/428

(56) References Cited

U.S. PATENT DOCUMENTS 5,624,798 A    4/1997    Yamamoto et al. ............ 435/6

FOREIGN PATENT DOCUMENTS

| EP | 603783 A | 6/1994 |
| EP | 837141 A | 4/1998 |
| JP | 9-040661 | 2/1997 |

*Primary Examiner*—T. A. Solola
(74) *Attorney, Agent, or Firm*—Fitzpatrick, Cella, Harper & Scinto (57) ABSTRACT

A novel pyrylium compound is represented by the general formula (I):

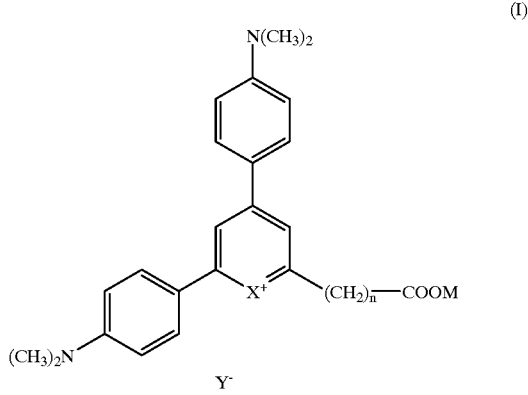

wherein X is oxygen or sulfur, Y[−] is a monovalent anion, n is an integer of 2 or 3, and M is hydrogen or an alkali metal. This pyrylium compound functions as a labeling agent by intermolecular bonding to nucleic acids, and as a fluorescence label having a chemical bond with the nucleic acids and an excitation wavelength in a visible light region.

3 Claims, 6 Drawing Sheets

PYRYLIUM COMPOUND, PROCESS FOR MAKING THE SAME, NUCLEIC ACID STAIN, AND LABELED NUCLEIC ACID

BACKGROUND OF THE INVENTION

1. Field of the Invention

The present invention relates to novel pyrylium compounds, methods for making the pyrylium compounds, and nucleic acids labeled with the pyrylium compounds. In particular, the present invention relates to a novel pyrylium compound which can be used as a label when a target nucleic acid is to be detected by optical means, to a process for making the pyrylium compound, and to a nucleic acid labeled with the pyrylium compound.

2. Description of the Related Art

Fluorescent dyes are widely used as labels for detecting target nucleic acids in biological samples. When the fluorescent dye is used as a label, a biological sample and the fluorescent dye are mixed and are allowed to stand in an environment in which the nucleic acid interacts with and links together the fluorescent dye on a molecular level. When the sample contains nucleic acids, the spectroscopic characteristics of the fluorescent dye change with such interactions. By detecting such changes, the nucleic acids in the sample can be identified or quantified. Interactions between the nucleic acids and the fluorescent dyes which have been conventionally used can be categorized as an intercalation in which fluorescent dyes are intercalated into base pairs of nucleic acids or as groove binding in which fluorescent dyes are incorporated along the groove of a double helix.

Examples of spectroscopic changes due to the interaction of the fluorescent dye include a shift of a peak wavelength in an absorption spectrum toward a shorter or longer wavelength, a change (increase or decrease) in absorbance, and a change (increase or decrease) in fluorescence intensity. When a target nucleic acid is detected by using a fluorescent dye as a label, changes (increase and decrease) in fluorescence intensity of the label are often used. Examples of known dyes interacting with the nucleic acids include acridine orange, proflavine, ethidium bromide, donomycin, actinomycin, and pyrylium salts. For example, pyrylium salts interacting with nucleic acids exhibit large shifts of absorption spectra toward longer wavelengths, and adequately large fluorescence intensity compared to the fluorescence intensity of the pyrylium salts in the free state. These two properties are advantageous for labeling of nucleic acids, and thus, the pyrylium salts have attracted attention as dyeing agents or labeling agents for nucleic acids. Many pyrylium salts interacting with nucleic acids have been proposed and synthesized, and properties thereof have been investigated.

One characteristic feature of the pyrylium salts is light absorption in the visible light region of the dyes. Since most of the above fluorescent dyes other than the pyrylium salts fluoresce, the excitation wavelength must be near the ultraviolet (UV) region. Japanese Unexamined Patent Application Publication No. 9-40661 by the present inventors discloses pyrylium compounds which have an absorption peak in a visible light region near 550 nm in an aqueous solvent so that the excitation wavelength is selected in the visible light region. When biological samples are living eukaryotic and prokaryotic cells, they will be damaged by UV irradiation of UV light as excitation light. Thus, the pyrylium salts for which the excitation light can be set within a visible light region are preferable since cell damage can be avoided.

The pyrylium salts have attracted attention as nucleic acid stains or fluorescence labeling agents. As described above, however, current interactions between the nucleic acids and the fluorescent dyes are classified into two types, that is, intercalation in which fluorescent dyes are intercalated between base pairs of nucleic acids, and groove binding in which fluorescent dyes are incorporated along the groove of the double helix. Japanese Unexamined Patent Application Publication No. 9-40661 by the present inventors discloses specific detection of target double-stranded nucleic acids using the above pyrylium compounds, and use of the pyrylium compounds as a probe by binding the compounds to a single stranded nucleic acid. For example, the pyrylium compounds represented by the following formulae (III) and (IV) are bonded to a single-stranded nucleic acid so that a carboxyl group bound to a pyrylium ring through a phenylene group forms an amido bond with an amino group which is incorporated into an end or a part of the single-stranded nucleic acid:

(III)

(IV)

SUMMARY OF THE INVENTION

One of the preferred properties of the probe comprising the pyrylium compound bound to a single-stranded nucleic acid is its ability to maintain its original absorbance and luminescence of the pyrylium compound even after binding to the single-stranded nucleic acid. Although the probes disclosed in the above patent are comparable to the unreacted pyrylium compounds with regard to specific detection of target nucleic acids, shifts in wavelength of the absorbance and the fluorescence were sometimes observed, and in the case where a shift was observed, it is necessary to re-calibrate the fluorescence detector.

Accordingly, it is an object of the present invention to provide a novel pyrylium compound which does not result in changes in optical characteristics, such as absorbance and fluorescence, when the pyrylium compound is bonded to a single-stranded nucleic acid, a process for making the pyrylium compound, and a labeled nucleic acid containing the pyrylium compound as a label.

The present inventors have researched changes in optical characteristics when a pyrylium compound having a carboxyl group which is bound to the pyrylium ring through a phenylene group is bonded to a single-stranded nucleic acid. As a result, the present inventors have hypothesized as follows. When an aromatic ring, such as a p-phenylene group or a 2-(p-phenylene)vinyl group, having a carboxyl group is directly bonded to a pyrylium ring having two 4-N,N-dimethylaminophenyl groups, some nucleic acids to be bonded affect the optical characteristics of the pyrylium pigment. Based on these results, the present inventors have attempted to bond of a pyrylium ring having two 4-N,N-dimethylaminophenyl groups to a carboxyl group with a non-conjugated group such as a methylene group therebetween. The present inventors have discovered that bonding of a single-stranded nucleic acid does not substantially affect the conjugated electronic state of the pyrylium ring and that the optical characteristics, such as fluorescence, of the unbonded pyrylium compound are maintained. The present invention has been accomplished according to these results.

According to an aspect of the present invention, there is provided a pyrylium compound represented by the following formula (I):

wherein X is oxygen or sulfur, $Y^-$ is a monovalent anion, n is an integer of 2 or 3, and M is hydrogen or an alkali metal.

According to another aspect of the present invention, there is provided a nucleic acid stain comprising the pyrylium compound represented by the formula (I).

According to another aspect of the present invention, there is provided a process for making the pyrylium compound represented by the formula (I), wherein X is oxygen, comprising the step of subjecting a cyclic anhydride represented by the following formula (II) to a condensation-cyclization reaction with 4-N,N-dimethylaminoacetophenone:

wherein n is an integer of 2 or 3.

According to a further aspect of the present invention, there is provided a labeled nucleic acid which is obtainable by reacting the pyrylium compound according to the above aspects with a single-stranded nucleic acid having a functional group capable of reacting with a carboxyl group.

According to another aspect of the present invention, there is provided a process for identifying a target double-stranded nucleic acid in a sample comprising the steps of:

(i) providing a sample in which a target single-stranded nucleic acid may exist;

(ii) mixing the sample with the above pyrylium compound;

(iii) irradiating the sample resulting from the step (ii) with light having a wavelength which is substantially equal to the maximum absorption wavelength when the pyrylium compound is intercalated into the double-stranded nucleic acid to excite the intercalated pyrylium compound; and (iv) ascertaining emission of fluorescence from the excited pyrylium compound to identify whether or not the target double-stranded nucleic acid exists in the sample.

Further objects, features and advantages of the present invention will become apparent from the following description of the preferred embodiments with reference to the attached drawings.

DESCRIPTION OF THE PREFERRED EMBODIMENTS

Novel Pyrylium Compound and Process for Making the Same

A pyrylium compound in accordance with the present invention is represented by the following formula (I):

(I)

wherein M is hydrogen, an alkali metal such as sodium or potassium, ammonium, or organic ammonium, X is oxygen or sulfur, and $Y^-$ is a monovalent anion, such as the iodide ion ($I^-$) or the perchlorate ion ($ClO_4^-$). When X is oxygen in this compound, the monovalent anion $Y^-$ is preferably selected from the iodide ion ($I^-$) and the perchlorate ion ($ClO_4^-$).

Spectroscopic characteristics of the pyrylium compound will now be described in detail.

The pyrylium compound in accordance with the present invention has a 4,6-bis-(4-N,N-dimethylaminophenyl) pyrylium ring or thiopyrylium ring, as a chromophore, represented by the formula (I'):

(I')

wherein X is oxygen or sulfur, n is an integer of 2 or 3, and the second position is replaced with an ω-carboxyl-substituted alkyl group. This pyrylium compound functions as an intercalate-type nucleic acid stain for double-stranded nucleic acids.

For example, when X is oxygen and the monovalent anion $Y^-$ is the iodide ion ($I^-$) or the perchlorate ion ($ClO_4^-$) in the formula (I), the pyrylium compound has a structure represented by the formula (III):

(III)

wherein $Y^-$ is the iodide ion ($I^-$) or the perchlorate ion ($ClO_4^-$) and n is an integer of 2 or 3. When this pyrylium compound (III) is irradiated with blue excitation light having a wavelength of 550 nm in the presence of double-stranded nucleic acids, a strong fluorescence is emitted near 630 nm. Fluorescence from this pyrylium compound (III) in the absence of the double-stranded nucleic acids is very slight compared to the above state. The fluorescent characteristics of this pyrylium compound are comparable to the fluorescent characteristics of the pyrylium compounds disclosed in Japanese Unexamined Patent Application Publication No. 9-40661 by the present inventors, for example, 2-methyl-4, 6-bis-(4-N,N-dimethylaminophenyl)pyrylium salt, and functions as an intercalate-type nucleic acid stain. That is, this pyrylium compound can be useful for specific detection of double-stranded nucleic acids and has superior characteristics as a nucleic acid stain. A thiopyrylium salt in which a thiopyrylium ring is substituted for the pyrylium ring in the pyrylium salt (III) also emits strong fluorescence in the presence of double-stranded nucleic acids and extremely slight fluorescence in the absence of the double-stranded nucleic acids. Thus, the thiopyrylium compound having a very similar structure also functions as an intercalate-type nucleic acid stain, like the pyrylium salt (III). Thus, the pyrylium compound in accordance with the present invention represented by the formula (III) maintains its function as a nucleic acid stain and has a carboxyl group.

Labeling of Nucleic Acid

Nucleic acids can be easily labeled by the carboxyl group of the pyrylium compound represented by the formula (I). Since the optical characteristics of the pyrylium compound are not substantially affected by the labeling of the nucleic acids, the pyrylium compound facilitates the designing and setting of a fluorescence detector and are significantly useful for correct identification and quantitative determination of the target nucleic acid.

Labeling of nucleic acids using the pyrylium compound represented by the formula (I) is achieved by reactive bonding of the carboxyl group of the pyrylium compound to a functional group which is present in parts of nucleic acids. Thus, the labeled nucleic acids in accordance with the present invention are nucleic acids having chemical bonds formed by condensation of the carboxyl group of the pyrylium compound represented by the formula (I) and the functional group which is present in parts of the nucleic acids. For example, labeled nucleic acids are obtained by the reaction of a pyrylium salt represented by the formula (I), wherein X is oxygen and the monovalent anion $Y^-$ is an iodide ion (I⁻) or perchlorate ion (ClO₄³¹), and nucleic acids having functional groups reactive with the carboxyl group. An example of a functional group of nucleic acids is the amino group which forms an amido bond by the reaction with the carboxyl group to label the nucleic acids with the pyrylium compound. In labeling of nucleic acids using the pyrylium compound represented by the formula (I), for example, a single-stranded DNA modified by an amino group is allowed to react with the pyrylium compound so as to form an amido bond between the carboxyl group of the pyrylium compound and the amino group of the single-stranded DNA. Nucleic acids, such as single-stranded DNA, do not have high solubility in organic solvents. Thus, it is preferable that the carboxyl group of the pyrylium compound be preliminarily esterified and be allowed to react with nucleic acids modified with an amino group in an aqueous solvent to form an amido bond.

The nucleic acids labeled by the above method can be identified by detecting absorption in the visible light region which is characteristic of the 4,6-bis-(4-N,N-dimethylaminophenyl)pyrylium ring or the 4,6-bis-(4-N,N-dimethylaminophenyl)thiopyrylium ring represented by the formula (I'). In the nucleic acids labeled by the above method, single-stranded DNA which has a specific base sequence and which is labeled with a stain acts as a DNA probe labeled with the stain. In such a DNA probe, as the single-stranded DNA having a specific base sequence, DNA fragments having a required base sequence which are generally synthesized using an automatic DNA synthesizer by solid-phase synthesis are often used.

As described above, the pyrylium compound represented by the formula (I) maintains its function as an intercalate-type nucleic acid stain. For example, the 4,6-bis-(4-N,N-dimethylaminophenyl) pyrylium ring exhibits a significantly high molar absorption coefficient. Thus, high solubility of the pyrylium compound is not required when the pyrylium compound is used as the intercalate-type nucleic acid stain. Since conventional pyrylium salts having no hydrophilic functional group have relatively low solubility in aqueous solvents, these are generally dissolved into aqueous solvents containing approximately 10% organic solvents, as in the conventional preparation of various nucleic acid stains. In contrast, the pyrylium compound represented by the formula (I) in accordance with the present invention has a carboxyl group which is highly hydrophilic and thus has high solubility in aqueous solutions. Thus, the organic solvent in the aqueous solution can be reduced to less than 10%.

The addition of organic solvents causes considerably decreased stability of the double helix structure in double-stranded nucleic acids contained in biological samples or causes transformation of the double-stranded DNA into different conformations, such as the A-type, B-type, and Z-type. When the biological sample is living cells, some organic solvents may damage the cells. However, use of the pyrylium compound represented by the formula (I) having the carboxyl group, which is highly hydrophilic, can drastically reduce the organic solvent content in aqueous solvents. As a result, the above effects of the organic solvents are moderated or avoided.

Among the pyrylium compounds represented by the formula (I), the pyrylium salts represented by the above formula (III) and corresponding thiopyrylium salts represented by the formula (IV) are preferred:

wherein Y⁻ is iodide ion (I⁻) or perchlorate ion (ClO₄⁻) and n is an integer of 2 or 3.

Synthesis of Pyrylium Compound Represented by Formula (I)

In a process for making the pyrylium compound in accordance with the present invention, for example, 4-N,N-dimethylaminoacetophenone may be allowed to react with glutaric anhydride where n=3 in the formula (I) or succinic anhydride where n=2 to form a pyrylium ring by condensation-cyclization. The thiopyrylium compound may be formed by the reaction of the above pyrylium compound with an alkali hydrosulfide so that sulfur is substituted for the oxygen in the pyrylium ring. More specifically, appropriate carboxylic anhydrides may be selected depending on the number of carbon atoms in the alkylene —(CH₂)ₙ– group of the pyrylium salt represented by the formula (III). For example, succinic anhydride is used where n=2, and glutaric anhydride is used where n=3. The cyclic acid anhydride and 4-N,N-dimethylaminoacetophenone are heated to, for example, approximately 120° C. in concentrated sulfuric acid to form a pyrylium ring by condensation-cyclization. If necessary, the anion Y⁻ may be exchanged to form another pyrylium salt. The thiopyrylium salt represented by the formula (IV) is prepared by the reaction of the corresponding pyrylium salt as an intermediate with sodium hydrosulfide so that a sulfur atom is substituted for the oxygen atom in the pyrylium ring. Also, the anion Y⁻ of the thiopyrylium salt may be exchanged to form another thiopyrylium salt.

The pyrylium compound of the present invention, the process for making the same, and spectroscopic characteristics in relation to the function as a nucleic acid stain thereof will now be described in more detail with reference to the following Examples.

EXAMPLES

Example 1

Preparation of 2-(3-Carboxypropyl)-4,6-bis(4-N,N-dimethylaminophenyl)pyrylium Iodide Pyrylium iodide (Compound 3) represented by the formula (10) was prepared as follows.

(10)

163 mg of 4-N,N-dimethylaminoacetophenone and 456 mg of glutaric anhydride were dissolved into 3 ml of concentrated sulfuric acid in an ice bath. The solution was heated with stirring to 120° C. in an oil bath for approximately 3 hours and was then cooled to room temperature. The solution was added to 100 ml of water and was stirred. To the solution, 50 ml of chloroform was added to remove unreacted 4-N,N-dimethylaminoacetophenone by extraction, and the aqueous layer was recovered. The chloroform extraction was repeated four times in total.

To the recovered aqueous layer, 1.50 g of sodium iodide was added, and the mixture was stirred and was cooled in a refrigerator overnight. A black precipitate of crude crystals of the target compound was recovered by filtration.

The crude compound was recrystallized using water. The yield of black crystal 2-(3-carboxypropyl)-4,6-bis(4-N,N-dimethylaminophenyl)pyrylium iodide was 66 mg.

Analytical Results $^1$H-NMR (400 MHz, DMSO): δ(ppm): 12.175(1H, s), 8.403(1H, s), 8.306(2H, d, J=9.03Hz), 8.193(2H, d, J=9.04Hz), 7.873(1H, s), 6.933(2H, d, J=7.02Hz), 6.910(2H, d, J=6.53Hz), 3.186(6H, s), 2.987(2H, m), 2.411(2H, t, J=7.03Hz), 2.054(2H, t, J=7.78Hz); IR (KBr); ν(cm$^{-1}$): 2361, 2340, 1646, 1611, 1589, 1505, 1383, 1275, 1201, 1169, 944, 820, 723.

Instead of the sodium iodide, an aqueous solution of perchloric acid was added to the recovered aqueous layer, and pyrylium perchlorate (Compound 4) represented by the formula (11) was prepared by the same procedures as with the sodium iodide.

(11)

Example 2

Preparation of 2-(3-Carboxypropyl)-4,6-bis(4-N,N-dimethylaminophenyl)thiopyrylium Iodide Pyrylium iodide (Compound 5) represented by the formula (12) was prepared as follows.

(12)

Into 1 ml of dimethyl sulfoxide (DMSO), 50 mg of the 2-(3-carboxypropyl)-4,6-bis(4-N,N-dimethylaminophenyl)pyrylium iodide, which was prepared in Example 1, was dissolved. To the solution, 0.3 ml of 1.5% sodium hydrosulfide was added. The mixture was stirred at room temperature for 5 minutes. Next, 0.04 ml of hydriodic acid was added to the solution, and the mixture was stirred for 5 minutes.

After dichloromethane extraction and purification using a silica gel column of the product according to conventional procedures, the product was recrystallized using an ethanol-ether (1:4 by volume) solvent mixture. The yield of the purified 2-(3-carboxypropyl)-4,6-bis(4-N,N-dimethylaminophenyl)thiopyrylium iodide (Compound 5) was 28 mg. The compound having a very similar structure to Compound 3 in Example 1 was identified by NMR and IR spectra.

Example 3

Preparation of 2-(2-Carboxyethyl)-4,6-bis(4-N,N-dimethylaminophenyl)pyrylium Iodide Pyrylium iodide (Compound 6) represented by the formula (13) was prepared as follows.

(13)

163 mg of 4-N,N-dimethylaminoacetophenone and 400 mg of succinic anhydride were dissolved into 3 ml of concentrated sulfuric acid in an ice bath. The solution was heated with stirring to 120° C. in an oil bath for approximately 3 hours and was then cooled to room temperature. The solution was added to 100 ml of water and was stirred. To the solution, 50 ml of chloroform was added to remove unreacted 4-N,N-dimethylaminoacetophenone by extraction, and the aqueous layer was recovered. The chloroform extraction was repeated four times in total.

To the recovered aqueous layer, 1.50 g of sodium iodide was added, and the mixture was stirred and was cooled in a refrigerator overnight. A black precipitate of crude crystals of the target compound was recovered by filtration. The crude compound was recrystallized using water. The yield of black crystal 2-(2-carboxyethyl)-4,6-bis(4-N,N-dimethylaminophenyl)pyrylium iodide was 52 mg.

Analytical Results $^1$H-NMR (400 MHz, DMSO): δ(ppm): 12.155(1H, s), 8.395(1H, s), 8.300(2H, d, J=9.03Hz), 8.188(2H, d, J=9.03Hz), 7.866(1H, s), 6.928(2H, d, J=8.03Hz), 6.908(2H, d, J=8.03Hz), 3.185(6H, s), 3.136(6H, s), 2.984(2H, t, J=7.53Hz), 2.410(2H, t, J=7.28Hz); IR (KBr); ν(cm$^{-1}$): 2361, 2341, 1649, 1609, 1587, 1499, 1376, 1272, 1200, 1164, 944, 820, 720.

Instead of the sodium iodide, an aqueous solution of perchloric acid was added to the recovered aqueous layer, and pyrylium perchlorate (Compound 7) represented by the formula (14) was prepared by the same procedures as with the sodium iodide.

(14)

Example 4

Preparation of 2-(2-carboxyethyl)-4,6-bis(4-N,N-dimethylaminophenyl)thiopyrylium Iodide Pyrylium iodide (Compound 8) represented by the formula (15) was prepared as follows.

(15)

Into 1 ml of dimethyl sulfoxide (DMS0), 50 mg of the 2-(2-carboxyethyl)-4,6-bis(4-N,N-dimethylaminophenyl)pyrylium iodide, which was prepared in Example 3, was dissolved. To the solution, 0.3 ml of 15% sodium hydrosulfide was added. The mixture was stirred at room temperature for 5 minutes. Next, 0.04 ml of hydriodic acid was added to the solution, and the mixture was stirred for 5 minutes.

After dichloromethane extraction and purification using a silica gel column of the product according to conventional procedures, the product was recrystallized using an ethanol-ether (1:4 by volume) solvent mixture. The yield of the purified 2-(2-carboxyethyl)-4,6-bis(4-N,N-dimethylaminophenyl)thiopyrylium iodide (Compound 8) was 26 mg. The compound having a very similar structure to Compound 7 in Example 3 was identified by NMR and IR spectra.

Example 5

Compound 3 prepared in Example 1 (2-(3-carboxypropyl)-4,6-bis(4-N,N-dimethylaminophenyl)pyrylium iodide) was dissolved into a 10 mM phosphate buffer solution (pH 7.0) to prepare Solution IA. A fraction of Solution IA was diluted to a final concentration of 3×10$^{-5}$ M, and the diluted solution was subjected to absorption spectrophotometry. The absorption spectrum is denoted by (A) in FIG. 1.

A DNA solution was prepared using salmon sperm DNA (mfd. by Sigma-Aldrich Co.) which was adequately purified according to a conventional method. A fraction of the DNA solution and a fraction of Solution IA were mixed to prepare Solution IB in which the final DNA concentration was 50 μg/ml and the final concentration of Compound 3 was 3×10$^{-5}$ M. A fraction of Solution IB was subjected to absorption spectrophotometry. The absorption spectrum is denoted by (B) in FIG. 1.

Figure 1:
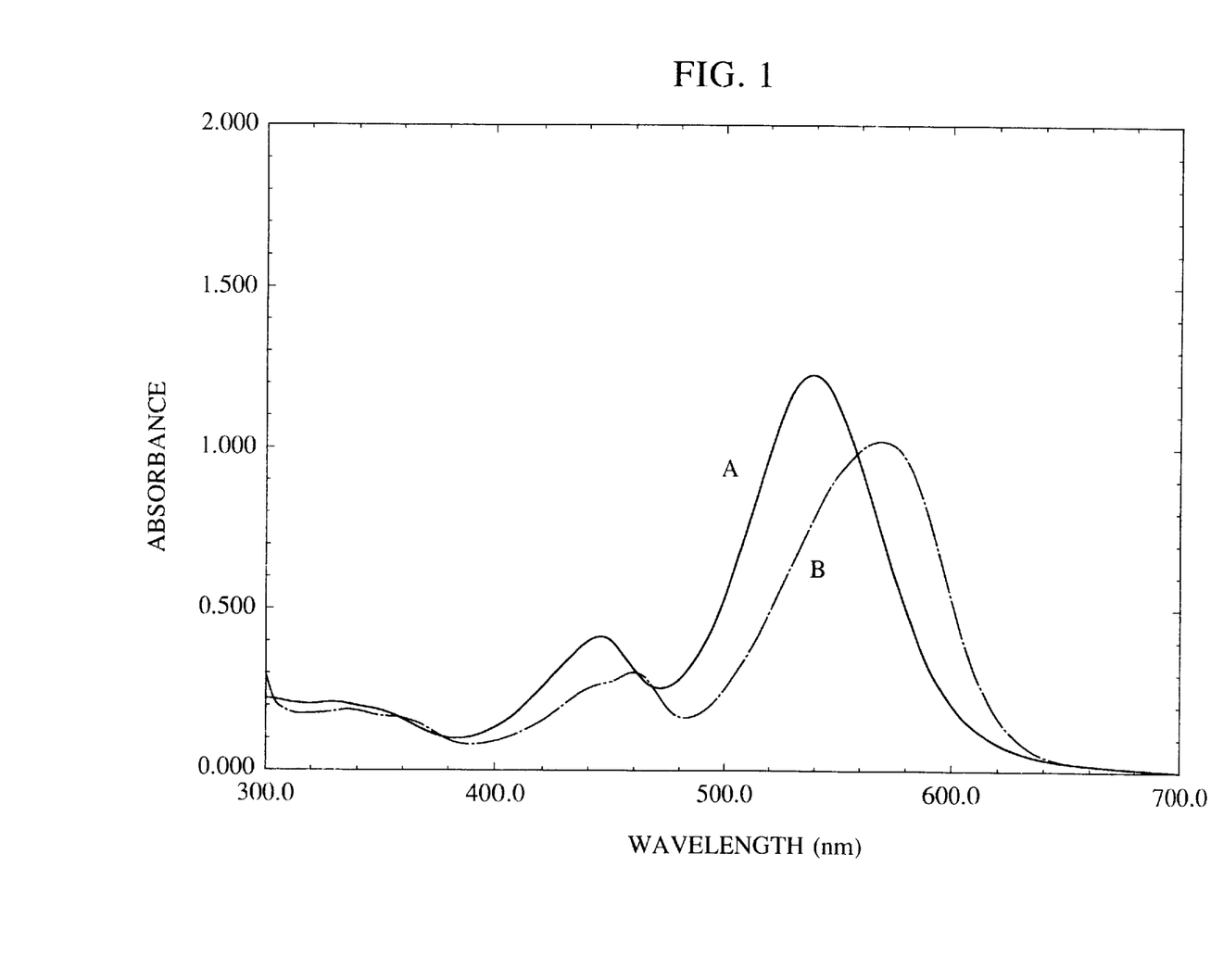
FIG. 1 shows an absorption spectrum (A) of a free pyrylium compound represented by the formula (10) and an absorption spectrum (B) of the pyrylium compound interacting with a double-stranded DNA.

With reference to spectrum (A) of Compound 3 and spectrum (B) of Solution IB in FIG. 1, the absorption bands of Solution IB are shifted to longer wavelengths by 30 nm and absorbance is decreased due to interaction between Compound 3 and the DNA. These changes can be attributed to the intercalative characteristics of Compound 3.

Figure 2:
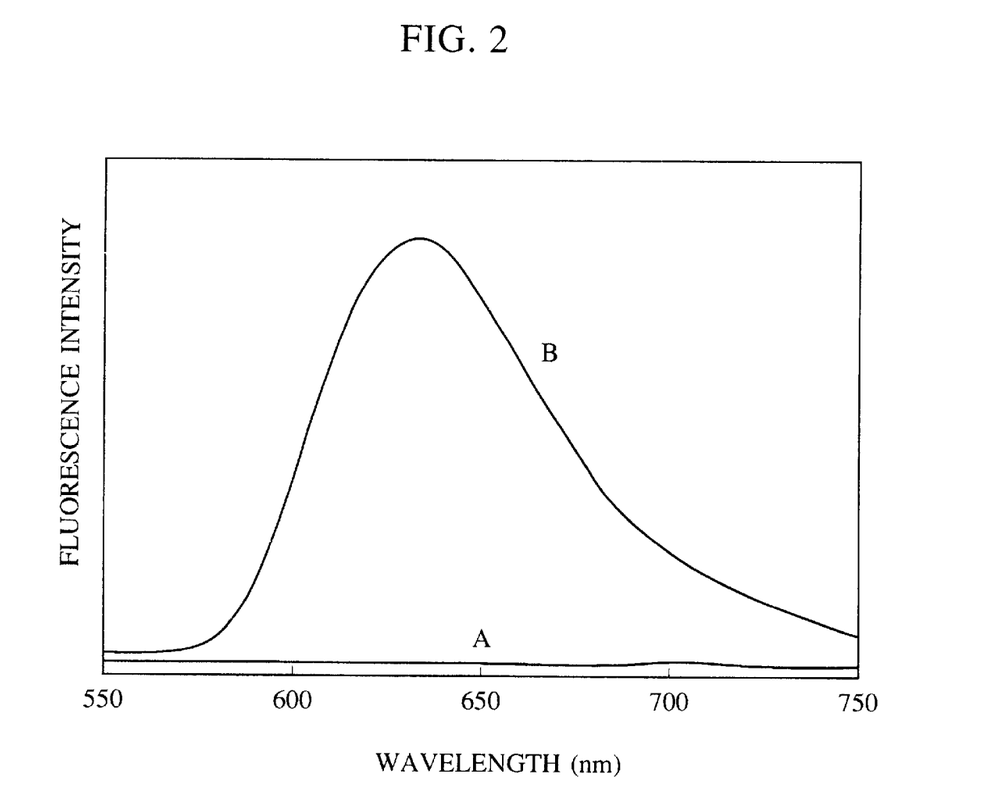
FIG. 2 shows a fluorescence spectrum (A) of a free a. pyrylium compound represented by the formula (10) and a fluorescence spectrum (B) of the pyrylium compound interacting with a double-stranded DNA.

A fraction of Solution IA and a fraction of Solution IB were diluted so that the concentration of Compound 3 was the same in these diluted solutions. The diluted solutions were subjected to conventional spectrofluorimetry by excitation light having a wavelength of 550 nm. FIG. 2 shows a fluorescence spectrum (A) of Solution IA and a fluorescence spectrum (B) of Solution IB. Solution IA ((A) in FIG. 2) not containing DNA does not fluoresce, whereas Solution IB ((B) in FIG. 2) containing DNA fluoresces intensely near 640 nm. The results show that the pyrylium compound in accordance with the present invention is useful for specific detection of double-stranded nucleic acid.

Example 6

Into 1 ml of dried dimethylformamide (DMF), 40 mg of Compound 3 prepared in Example 1 and 46 mg of N-hydroxysuccinimide were dissolved. The completely dissolved solution was cooled in an ice bath. To the solution, 80 mg of N,N-dicyclohexylcarbodiimide (DCC) was added, and the mixture was stirred in the dark for 24 hours in total, that is, in an ice bath for 2 hours and then at room temperature for 22 hours. After DCC urea floating on the solution was removed by a membrane filter, the solution was added dropwise to approximately 50 ml of diethyl ether. The precipitate was recovered and washed with approximately 50 ml of diethyl ether. The washing procedure was repeated several times. A black powder of Compound 9 represented by the formula (16) was prepared. The powder was vacuum-dried using a vacuum pump.

(16)

An 18-mer oligonucleotide having a bonded amino linker at the 5' end and having the following base sequence (Sequence 1) was synthesized by an automatic DNA synthesizer.

Sequence 1: 5'-TGTAAAACGACGGCCAGT-3'

The 18-mer oligonucleotide was cleaved from a CPG support, was deprotected according to a conventional method, and was purified by high performance liquid chromatography (HPLC).

Into 100 μl of deionized water, 330 μg of the oligonucleotide having the amino linker at the 5' end was dissolved, and 16 μl of a 1M phosphate buffer solution (pH=7.0) was added thereto. Next, 60 μl of a 50 mM Compound 6 in acetonitrile solution was added to the solution, and the mixture was allowed to react at 40° C. for 24 hours. The product was roughly purified using a gel permeation column NAP-25 for DNA made by Pharmacia Biotech and was then finely purified by HPLC. The purified product was passed through the above gel permeation column to form a DNA probe labeled with Compound 3 represented by the formula (17) by desalination.

(17)

Figure 3:
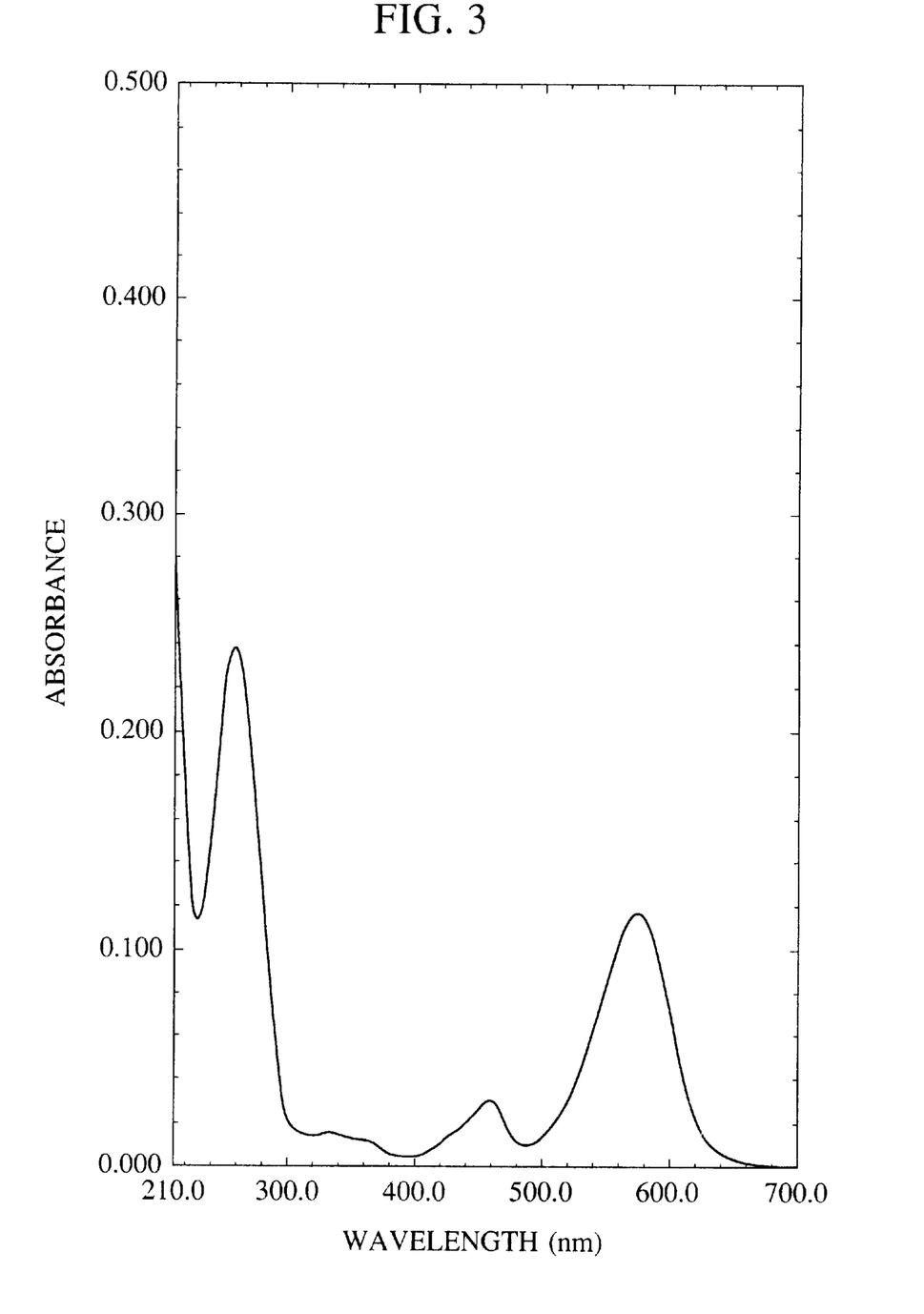
FIG. 3 shows an absorption spectrum of a DNA probe labeled with a pyrylium compound represented by the formula (10)

FIG. 3 shows an absorption spectrum of the DNA probe labeled with Compound 3. The Compound 3 as the labeling dye has absorption bands near 570 nm and 460 nm, whereas the unlabeled DNA has an absorption band near 260 nm. The absorption spectrum shown in FIG. 3 also has substantially the same absorption bands, each having the absorbance which is substantially equal to the absorbance estimated from the analogy with the molar absorption coefficients of Compound 3 and the DNA. The results show that the Compound 3 and the DNA are bonded to each other to form a DNA probe having the structure represented by the formula (17). Accordingly, the pyrylium compound in accordance with the present invention exhibits substantially no change in optical characteristics due to bonding to nucleic acids.

Example 7

Compound 6 prepared in Example 3 (2-(2-carboxyethyl)-4,6-bis(4-N,N-dimethylaminophenyl)pyrylium iodide) was dissolved into a 10 mM phosphate buffer solution (pH 7.0) to prepare Solution IIA. A fraction of Solution IIA was diluted to a final concentration of $3 \times 10^{-5}$ M, and the diluted solution was subjected to absorption spectrophotometry. The absorption spectrum is denoted by (A) in FIG. 4.

A DNA solution was prepared using salmon sperm DNA (Sigma-Aldrich Co.) which was adequately purified according to a conventional method. A fraction of the DNA solution and a fraction of Solution IIA were mixed to prepare Solution IIB in which the final DNA concentration was 50 μg/ml and the final concentration of Compound 6 was $3 \times 10^{-5}$ M. A fraction of Solution IIB was subjected to absorption spectrophotometry. The absorption spectrum is denoted by (B) in FIG. 4.

Figure 4:
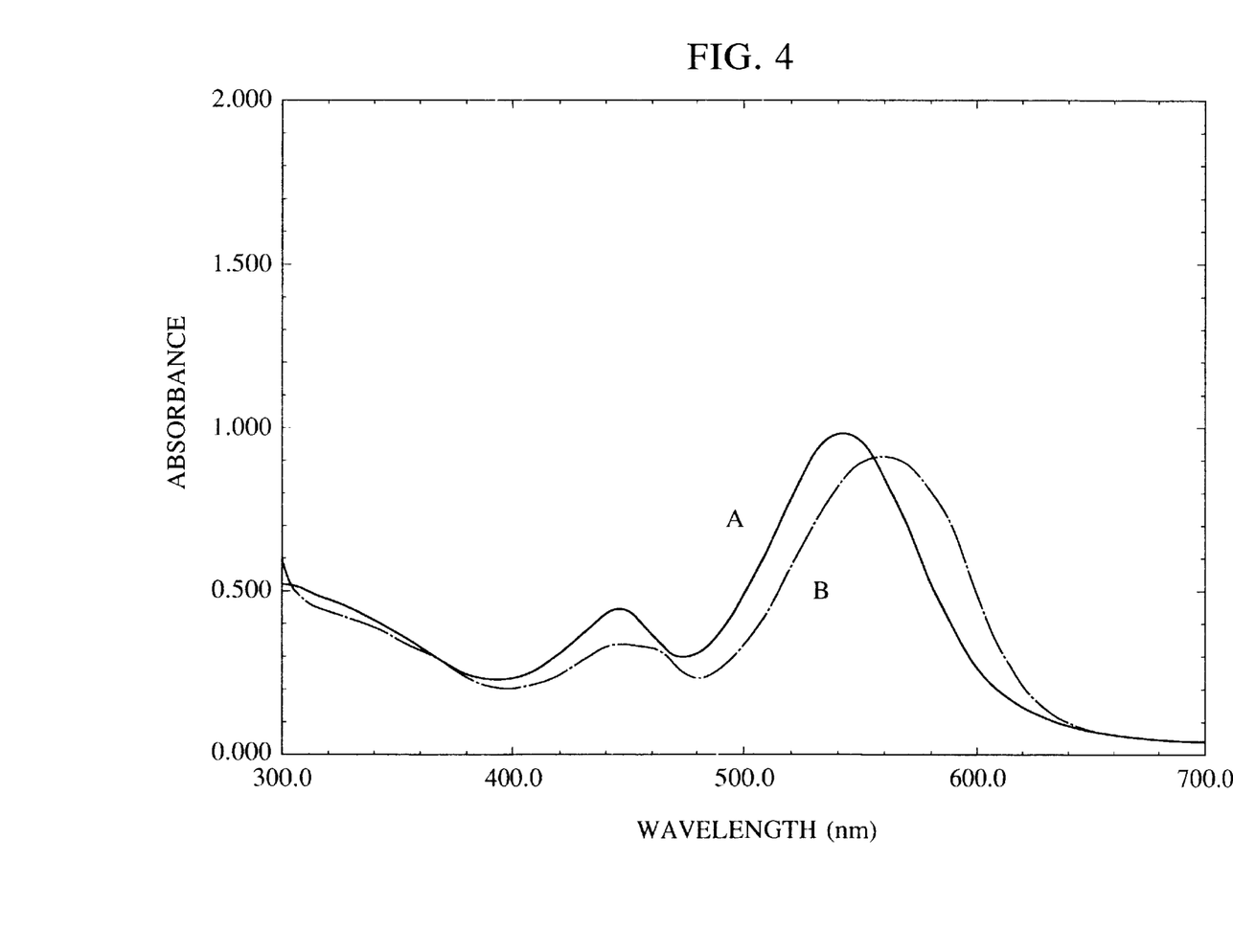
FIG. 4 shows an absorption spectrum (A) of a free pyrylium compound represented by the formula (13) and an absorption spectrum (B) of the pyrylium compound interacting with a double-stranded DNA.

With reference to spectrum (A) of Compound 6 and spectrum (B) of Solution IIB in FIG. 4, the absorption bands of Solution IIB are shifted to longer wavelengths by 30 nm and absorbance is decreased due to interaction between Compound 6 and the DNA. These changes can be attributed to intercalative characteristics of Compound 6.

Figure 5:
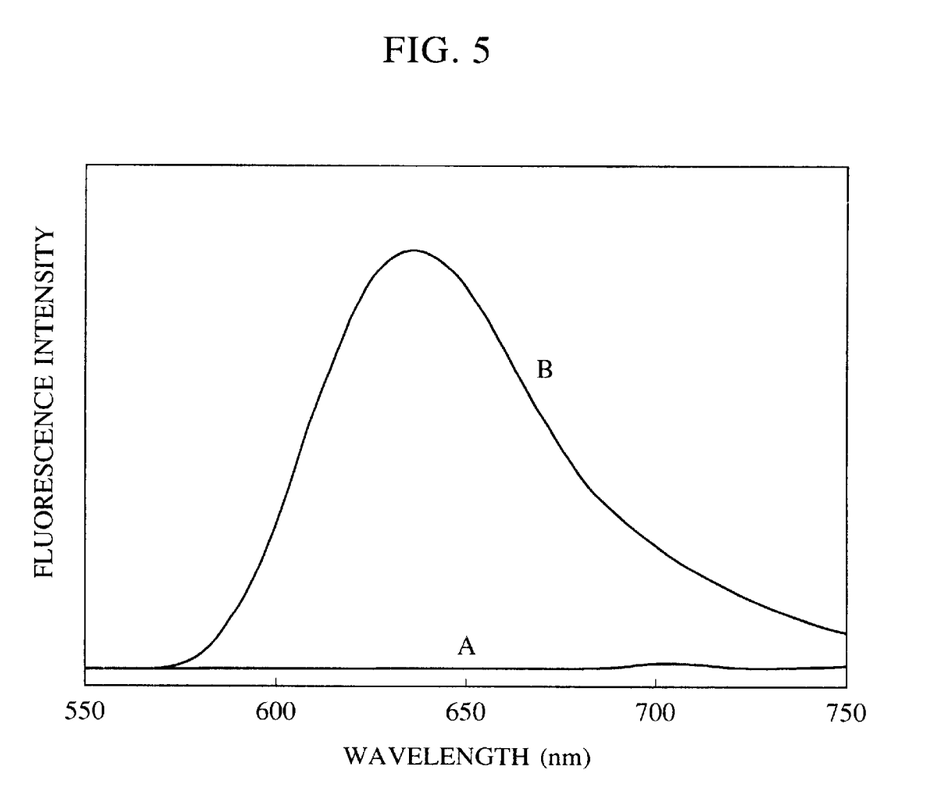
FIG. 5 shows a fluorescence spectrum (A) of a free pyrylium compound represented by the formula (13) and a fluorescence spectrum (B) of the pyrylium compound interacting with a double-stranded DNA.

A fraction of Solution IIA and a fraction of Solution IIB were diluted so that the concentration of Compound 6 was the same in these diluted solutions. The diluted solutions were subjected to conventional spectrofluorimetry by excitation light having a wavelength of 550 nm. FIG. 5 shows a fluorescence spectrum (A) of Solution IIA and a fluorescence spectrum (B) of Solution IIB. Solution IIA ((A) in FIG. 5) which does not contain DNA does not fluoresce, whereas Solution IIB ((B) in FIG. 5) which contains DNA fluoresces intensely near 640 nm.

Example 8

Into 1 ml of dried DMF, 38 mg of Compound 6 prepared in Example 3 and 46 mg of N-hydroxysuccinimide were dissolved. The completely dissolved solution was cooled in an ice bath. To the solution, 80 mg of N,N-dicyclohexylcarbodiimide (DCC) was added, and the mixture was stirred in the dark for 24 hours in total, that is, in an ice bath for 2 hours and then at room temperature for 22 hours. After DCC urea floating on the solution was removed by a membrane filter, the solution was added dropwise to approximately 50 ml of diethyl ether. The precipitate was recovered and washed with approximately 50 ml of diethyl ether. The washing procedure was repeated several times. A black powder of Compound 10 represented by the formula (18) was prepared. The powder was vacuum-dried using a vacuum pump.

(18)

An 18-mer oligonucleotide having a bonded amino linker at the 5' end and having the following base sequence (Sequence 1) was synthesized by an automatic DNA synthesizer.

Sequence 1: 5'-TGTAAAACGACGGCCAGT-3'

The 18-mer oligonucleotide was cleaved from a CPG support, was deprotected according to a conventional method, and was purified by high performance liquid chromatography (HPLC).

Into 100 μl of deionized water, 330 μg of the oligonucleotide having the amino linker at the 5' end was dissolved, and 16 μl of a 1M phosphate buffer solution (pH=7.0) was added thereto. Next, 60 μl of a 50 mM Compound 10 in acetonitrile solution was added to the solution, and the mixture was allowed to react at 40° C. for 24 hours. The product was roughly purified using a gel permeation column NAP-25 for DNA made by Pharmacia Biotech AB and was then finely purified by HPLC. The purified product was passed through the above gel permeation column to form a DNA probe labeled with Compound 9 represented by the formula (19) by desaltation.

(19)

Figure 6:
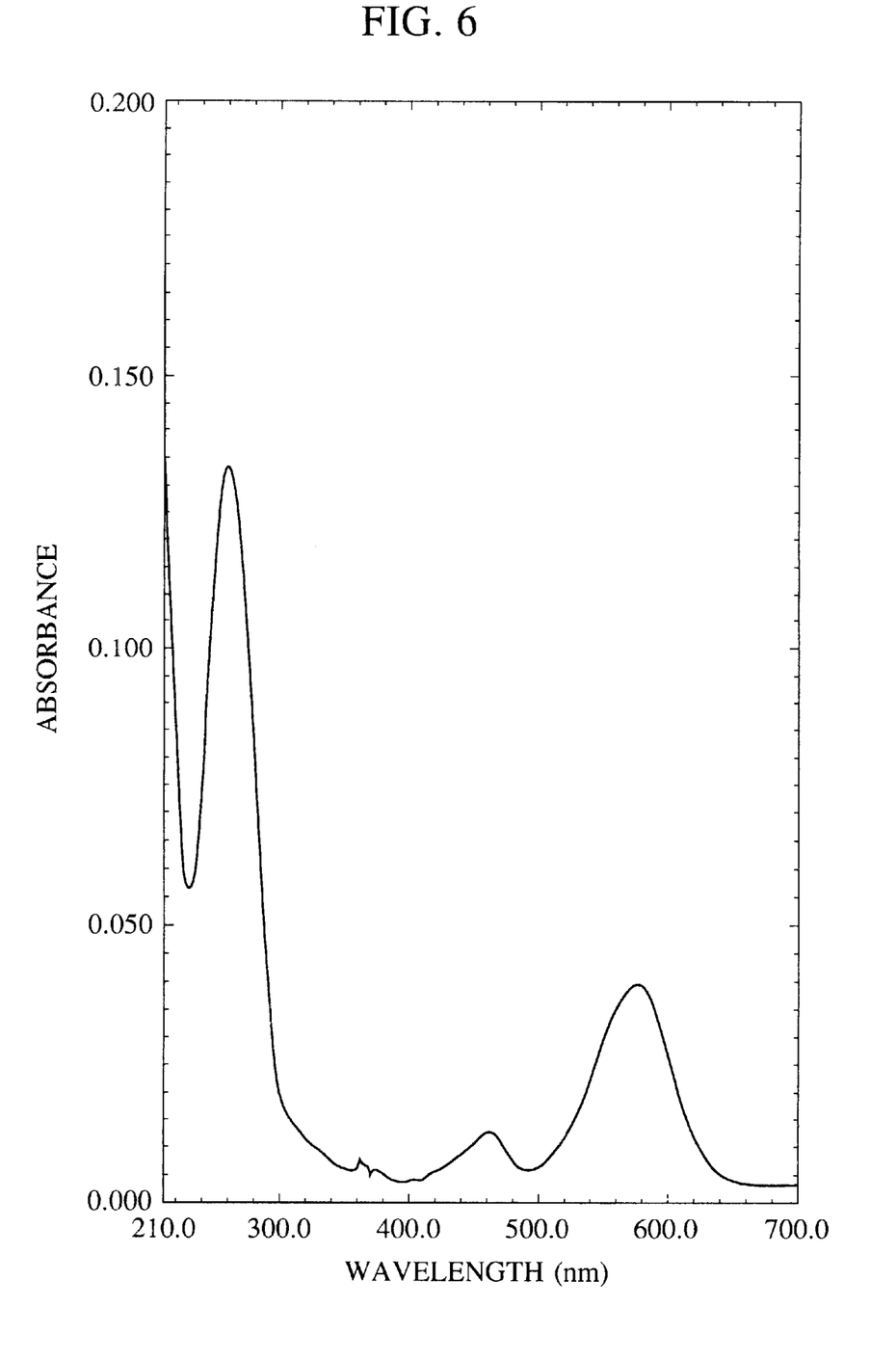
FIG. 6 shows an absorption spectrum of a DNA probe labeled with a pyrylium compound represented by the formula (13).

FIG. 6 shows an absorption spectrum of the DNA probe labeled with Compound 6. The Compound 6 as the labeling dye has absorption bands near 570 nm and 460 nm, whereas the unlabeled DNA has an absorption band near 260 nm. The absorption spectrum shown in FIG. 6 also has substantially the same absorption bands, each having the absorbance which is substantially equal to the absorbance estimated from the analogy with the molar absorption coefficients of Compound 6 and the DNA. The results show that the Compound 6 and the DNA are bonded to each other to form the DNA probe having the structure represented by the formula (19).

According to the present invention, the pyrylium compound having a novel structure maintains spectroscopic characteristics of the pyrylium or thiopyrylium ring as a chromophore of a labeling dye, and particulary, the 4,6-bis(4-N,N-dimethylaminophenyl)pyrylium or thiopyrylium ring and has a hydrophilic carboxyl group bonded to a pyrylium or thiopyrylium ring with a nonconjugated system therebetween. The introduced hydrophilic carboxyl group is chemically reactive with a variety of nucleic acids. Thus, nucleic acids labeled with the pyrylium compound of the present invention, for example, a labeled DNA probe readily prepared. In addition, the pyrylium compound of the present invention can be used as an intercalate-type nucleic acid stain for double-stranded nucleic acids. The introduced hydrophilic carboxyl group enhances solubility of the pyrylium compound and can reduce the amount of organic solvent which is added to an aqueous solvent, as compared to conventional compounds used as nucleic acid stains which have poor solubility in aqueous solutions and require approximately 10% organic solvents.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:
1. A pyrylium compound represented by the following formula (I):

(I)

wherein X is oxygen or sulfur, Y⁻ is a monovalent anion, n is an integer of 2 or 3, and M is hydrogen or an alkali metal.

2. A pyrylium compound according to claim 1, wherein, in the formula (I), X is oxygen and Y⁻ is iodide ion or perchlorate ion.

3. A process for making the pyrylium compound represented by the formula (I):

(I)

wherein X is oxygen, Y⁻ is a monovalent anion, n is an integer of 2 or 3, and M is hydrogen or an alkali metal, comprising the step of subjecting a cyclic anhydride represented by the following formula (II) to a condensation-cyclization reaction with 4-N,N-dimethylaminoacetophenone:

(II)

wherein n is an integer of 2 or 3.

* * * * *

UNITED STATES PATENT AND TRADEMARK OFFICE
CERTIFICATE OF CORRECTION

PATENT NO. : 6,384,237 B1
DATED : May 7, 2002
INVENTOR(S) : Tomohiro Suzuki et al.

It is certified that error appears in the above-identified patent and that said Letters Patent is hereby corrected as shown below:

Column 1,
Line 65, "of UV light" should read -- used --.

Column 2,
Line 12, "single stranded" should read -- single-stranded --;
Line 64, "case" should read -- cases --.

Column 3,
Line 16, "of" should be deleted.

Column 4,
Line 37, "a." should be deleted.

Column 7,
Line 1, "($ClO_4^{31}$)," should read -- ($ClO_4^-$), --.

Column 9,
Line 32, close up right margin;
Line 33, close up left margin.

Column 16,
Line 43, "probe" should read -- probe, are --.

Signed and Sealed this

Eighth Day of October, 2002

Attest:

JAMES E. ROGAN
*Attesting Officer*     *Director of the United States Patent and Trademark Office*